United States Patent
Rajamohan et al.

(10) Patent No.: US 7,524,644 B2
(45) Date of Patent: Apr. 28, 2009

(54) METHOD FOR OXYGEN REGULATED PRODUCTION OF RECOMBINANT STAPHYLOKINASE

(75) Inventors: Govindan Rajamohan, Chandigarh (IN); Monika Dahiya, Chandigarh (IN); Ranjana Pathania, Chandigarh (IN); Kanak Lata Dikshit, Chandigarh (IN)

(73) Assignee: Council of Scientific and Industrial Research, New Delhi (IN)

( * ) Notice: Subject to any disclaimer, the term of this patent is extended or adjusted under 35 U.S.C. 154(b) by 278 days.

(21) Appl. No.: 10/814,850

(22) Filed: Mar. 31, 2004

(65) Prior Publication Data

US 2005/0019862 A1 Jan. 27, 2005

Related U.S. Application Data

(60) Provisional application No. 60/459,439, filed on Apr. 1, 2003.

(51) Int. Cl.
*C12N 9/70* (2006.01)
*C12P 21/04* (2006.01)
*C07H 21/04* (2006.01)
*C12N 15/00* (2006.01)

(52) U.S. Cl. .................. 435/69.1; 435/216; 435/252.3; 435/320.1; 435/252.33; 536/23.2

(58) Field of Classification Search .............. None
See application file for complete search history.

(56) References Cited

OTHER PUBLICATIONS

Rajamohan G. et al., Role of the N-terminal region of staphylokinase (SAK): evidence for the participation of the N-terminal region of SAK in the enzyme-substrate complex formation, FEBS Letters, 2000, 474, 151-158.*
Sako T. et al. Cloning and expression of the staphylokinase gene of *Staphylococcus aureus* in *Escherichia coli*, Mol. Gen. Genet. 190, 271-277, 1983; abstract.*

* cited by examiner

*Primary Examiner*—Nashaat T Nashed
*Assistant Examiner*—Mohammad Younus Meah
(74) *Attorney, Agent, or Firm*—Ladas and Parry LLP

(57) ABSTRACT

The present invention relates to a nucleotide sequence of expression cassette OXY-1 of SEQ ID No. 1, a modified staphylokinase SAK-2 gene of SEQ ID No. 2, a peptide sequence of modified staphylokinase SAK-2 gene, of SEQ ID No. 3, three plasmids having International Deposition Nos. BPL-0019, BPL-0020, and BPL-0021, and their corresponding three recombinant *E. Coli*; also invention relates to a process for over-producing staphylokinase and its analogues by modulating level of oxygen of its growth medium in a host system, and lastly, a method of dissolving blood clot in a subject in need thereof.

11 Claims, 10 Drawing Sheets

Map of pRM1

Figure 1:
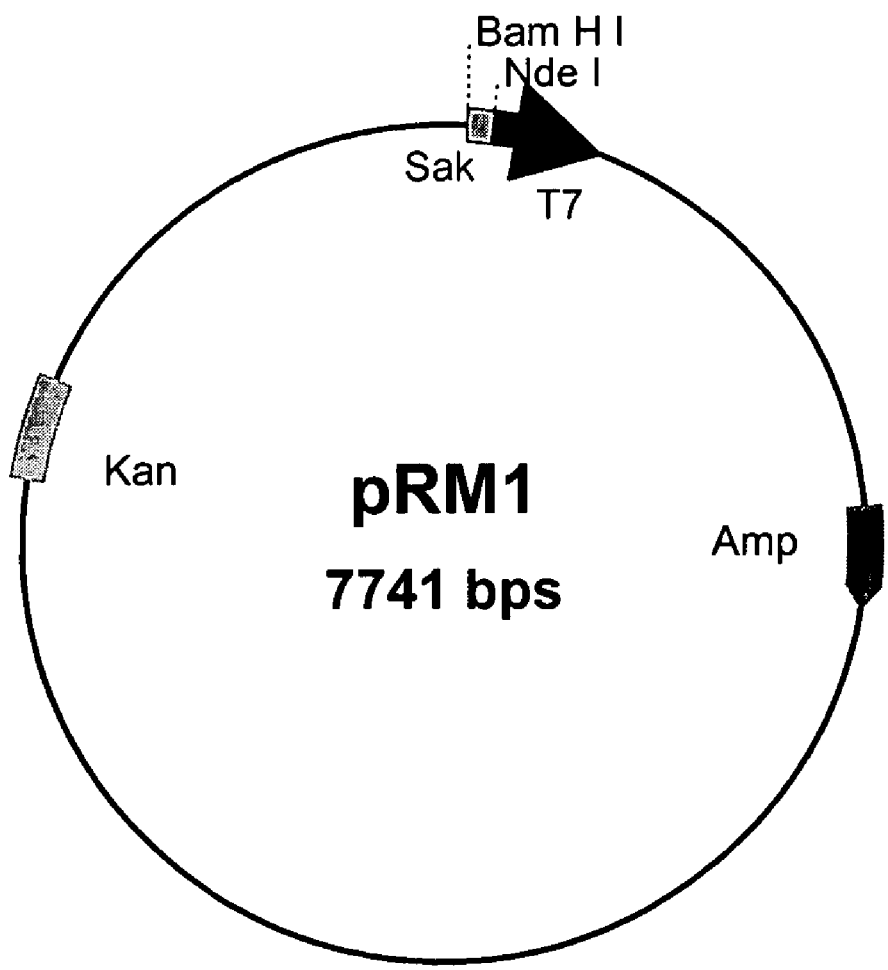

Fig. 2 Sequence of oligonucleotide to construct the protein expression cassette 1. 5' GATCAAGCTTATCATCGATAAGCTTACAGGACGCTGGGTTAAAA GTATTT -3" ( 51 mer ) PEC 1
2. 5"- ATCTTATTGACCTCTCAAAACTTAATCCACATCAAAACTCAAATAC TTTTAACCC -3" ( 55 mer ) PEC 2
3. 5"-AGAGGTCAATAAGATTATAATATGTGATGCTTCACAATTCTGATG TATGGCAAAA -3" ( 55 mer ) PEC 3
4. 5"-ATGAGGTCTTCCTTAAGTTCATTATTATGGTTTTGCCATACATCA GAATT -3" ( 50 mer ) PEC 4

Fig. 3 Complete nucleotide sequence of expression cassette, OXY-1

GATCAAGCTTATCATCGATAAGCTTACAGGACGCTGGGTTAAAAGTATTTG
AGTTTTGATGTGGATTAAGTTTTGAGAGGTCAATAAGATTATAATATGTGA
TGCTTCACAATTCTGATGTATGGCAAAACCATAATAATGAACTTAAGGAAG
ACCTCATG (161 mer )

Fig.4 Nucleotide sequence of SAK gene

TCAAGTTCATTCGACAAAGGAAAATATAAAAAGGGCGATGACGCGAGTTA
TTTTGAACCAACAGGCCCGTATTTGATGGTAAATGTGACTGGAGTTGATGG
TAAAGGAAATGAATTGCTATCCCCTCATTATGTCGAGTTTCCTATTAAACC
TGGGACTACACTTACAAAAGAAAAAATTGAATACTATGTCGAATGGGCAT
TAGATGCGACAGCATATAAAGAGTTTAGAGTAGTTGAATTAGATCCAAGC
GCAAAGATCGAAGTCACTTATTATGATAAGAATAAGAAAAAGAAGAAAC
GAAGTCTTTCCCTATAACAGAAAAAGGTTTTGTTGTCCCAGATTTATCAGA
GCATATTAAAAACCCTGGATTCAACTTAATTACAAAGGTTGTTATAGAAAA
GAAATAA (411 nucleotides )

Fig. 5 Nucleotide sequence encoding SAK 1 protein

GAACTTAAGGAAGATATACATATGTCAAGTTCATTCGACAAAGGAAAATA
TAAAAAGGGCGATGACGCGAGTTATTTTGAACCAACAGGCCCGTATTTGAT
GGTAAATGTGACTGGAGTTGATGGTAAAGGAAATGAATTGCTATCCCCTCA
TTATGTCGAGTTTCCTATTAAACCTGGGACTACACTTACAAAAGAAAAAAT
TGAATACTATGTCGAATGGGCATTAGATGCGACAGCATATAAAGAGTTTA
GAGTAGTTGAATTAGATCCAAGCGCAAAGATCGAAGTCACTTATTATGATA
AGAATAAGAAAAAGAAGAAACGAAGTCTTTCCCTATAACAGAAAAAGGT
TTTGTTGTCCCAGATTTATCAGAGCATATTAAAAACCCTGGATTCAACTTA
ATTACAAAGGTTGTTATAGAAAAGAAATAAAACAAAATAGTTGTTTATTAT
AGAAAGTAATGTCTTGATTGAATATGTGTAGTGAAATTATCTTTCATCAAA
TTCTCATTCATGCACGAATGGTTCTGCCCCACCTAATCAGATATTACGTGA
CTTATGGGGAGAAATCAGTTTGGATAAAAGTGGAGGATCCAGTAGCCG
606 nucleotides)

Oligo's :

SAK-3 primer :

5'- GAACTTAAGGAAGATATACATATGTCAAGTTCATTCGACAAAGGA-3'

(45 mer )

SAK-2 primer

5'- CGGCTACTGGATCCTCCACTTTTATCCAAACTGATTT -3' ( 38 mer )

Fig. 6 Nucleotide sequence encoding SAK-2 protein

GAACTTAAGCATATGAAAGGAAAATATAAAAAGGGCGATGACGCGAGTTA
TTTTGAACCAACAGGCCCGTATTTGATGGTAAATGTGACTGGAGTTGATGG
TAAAGGAAATGAATTGCTATCCCCTCATTATGTCGAGTTTCCTATTAAACC
TGGGACTACACTTACAAAAGAAAAAATTGAATACTATGTCGAATGGGCAT
TAGATGCGACAGCATATAAAGAGTTTAGAGTAGTTGAATTAGATCCAAGC
GCAAAGATCGAAGTCACTTATTATGATAAGAATAAGAAAAAGAAGAAAC
GAAGTCTTTCCCTATAACAGAAAAAGGTTTTGTTGTCCCAGATTTATCAGA
GCATATTAAAAACCCTGGATTCAACTTAATTACAAAGGTTGTTATAGAAAA
GAAA TAAAACAAAATAGTTGTTTATTATAGAAAGTAATGTCTTGATTGAAT
ATGTGTAGTGAAATTATCTTTCATCAAATTCTCATTCATGCACGAATGGTTC
TGCCCCACCTAATCAGATATTACGTGACTTATGGGGAGAAATCAGTTTGGA
TAAAAGTGGAGGATCCAGTAGCCG ( 582 nucleotides )

Oligo's :

SAK-4 primer :

5'- GAACTTAAGCATATGGCTGGAGCTTATAAAAAGGGC -3' (36 mer)

SAK-2 primer :

2. 5'- CGGCTACTGGATCCTCCACTTTTATCCAAACTGATTT -3' (37 mer)

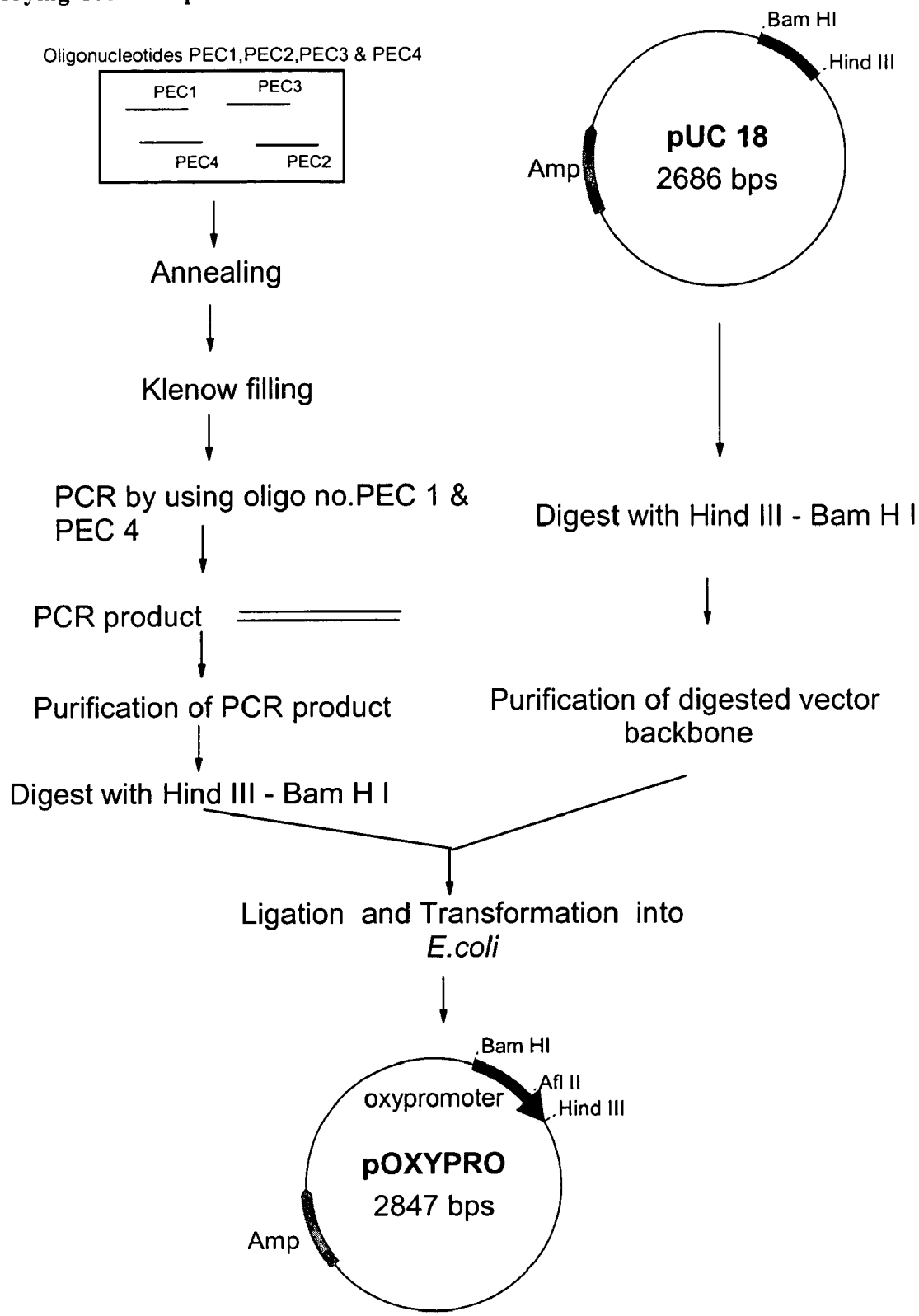
Fig. 7 Schematic representation of construction of plasmid, pOXYPRO, carrying OXY-1 expression cassette.

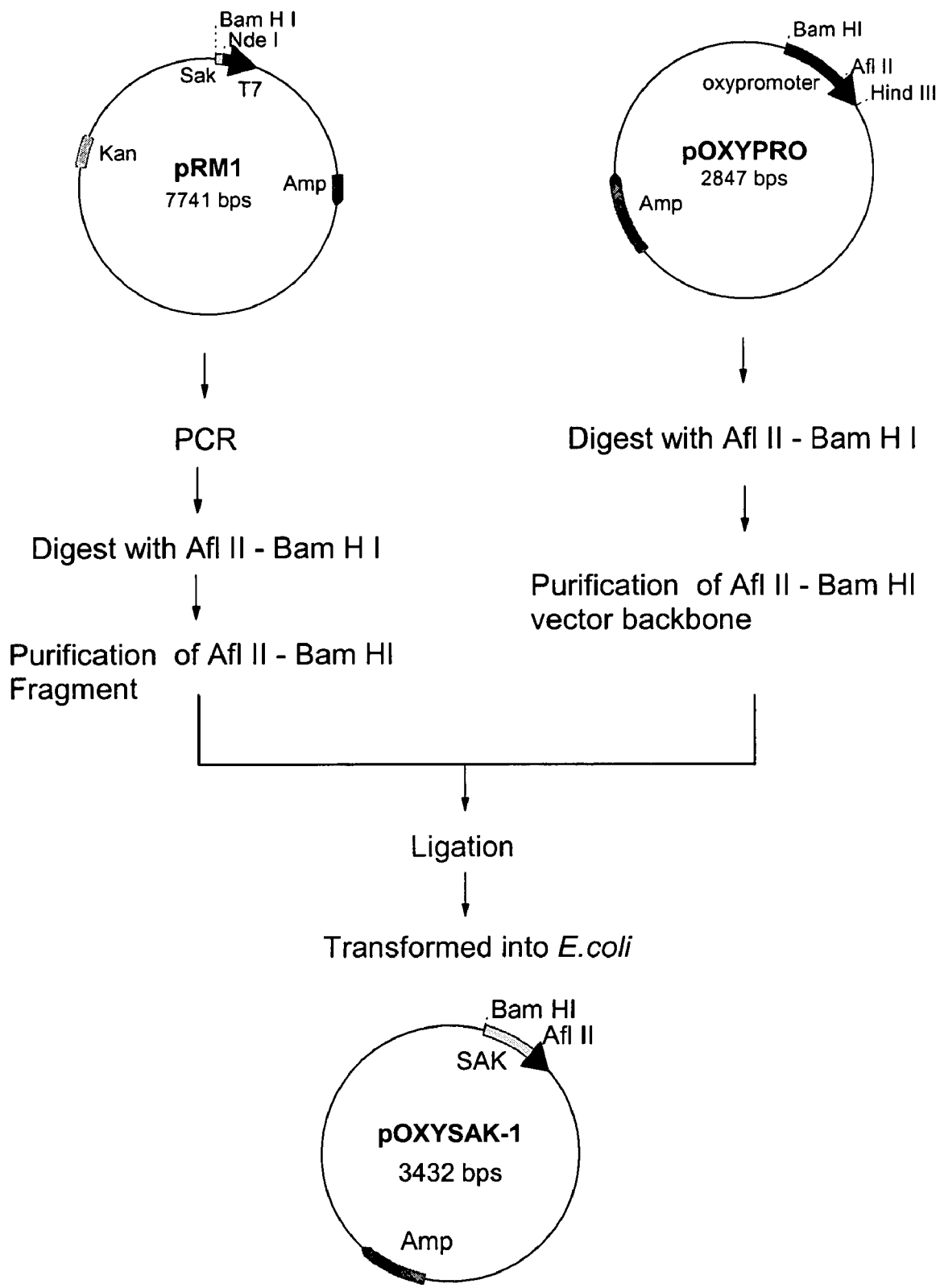
Fig. 8 Construction and map of plasmid, pOXYSAK-1 containing SAK-1 gene under OXY-1 expression cassette.

Fig.9 Construction and map of plasmid, pOXYSAK-2 containing SAK-2 gene under OXY-1 expression cassette.
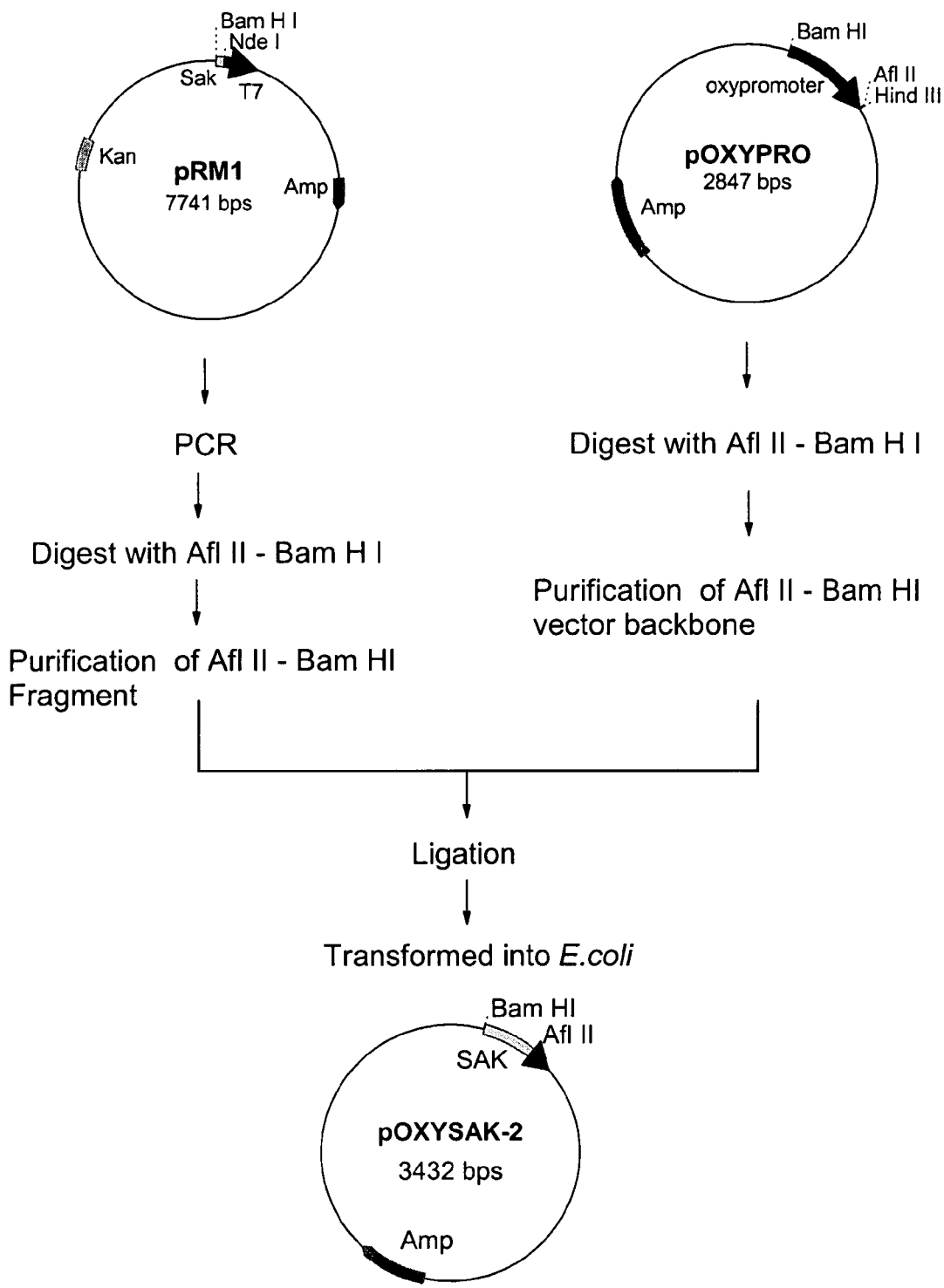
Fig.10 Sequences of SAK, SAK-1 and SAK-2 genes.

Fig. 10A Sequences encoding SAK, SAK-1 and SAK-2 proteins

```
SAK                          TCAAGTTCATTCGACAAAGGAAA
SAK-1 GAACTTAAGGAAGATATACATATGTCAAGTTCATTCGACAAAGGAAA
SAK-2                GAACTTAAGCATATG g c tGGA gc

SAK   ATATAAAAGGGCGATGACGCGAGTTATTTTGAACCAACAGGCCCGT
SAK-1 ATATAAAAGGGCGATGACGCGAGTTATTTTGAACCAACAGGCCCGT
SAK-2 t TATAAAAAGGGCGATGACGCGAGTTATTTTGAACCAACAGGCCCGT

SAK   ATTTGATGGTAAATGTGACTGGAGTTGATGGTAAAGGAAATGAATTG
SAK-1 ATTTGATGGTAAATGTGACTGGAGTTGATGGTAAAGGAAATGAATTG
SAK-2 ATTTGATGGTAAATGTGACTGGAGTTGATGGTAAAGGAAATGAATTG

SAK   CTATCCCCTCATTA TGTCGAGTTTCCTATTAAACCTGGGACTACACT
SAK-1 CTATCCCCTCATTA TGTCGAGTTTCCTATTAAACCTGGGACTACACT
SAK-2 CTATCCCCTCATTA TGTCGAGTTTCCTATTAAACCTGGGACTACACT

SAK   TACAAAAGAAAAAATTGAATACTATGTCGAATGGGCATTAGATGCGA
SAK-1 TACAAAAGAAAAAATTGAATACTATGTCGAATGGGCATTAGATGCGA
SAK-2 TACAAAAGAAAAAATTGAATACTATGTCGAATGGGCATTAGATGCGA

SAK   CAGCATATAAAGAGTTTAGAGTAGTTGAATTAGATCCAAGCGCAAAG
SAK-1 CAGCATATAAAGAGTTTAGAGTAGTTGAATTAGATCCAAGCGCAAAG
SAK-2 CAGCATATAAAGAGTTTAGAGTAGTTGAATTAGATCCAAGCGCAAAG

SAK   ATCGAAGTCACTTATTATGATAAGAATAAGAAAAAAGAAGAAACGAA
SAK-1 ATCGAAGTCACTTATTATGATAAGAATAAGAAAAAAGAAGAAACGAA
SAK-2 ATCGAAGTCACTTATTATGATAAGAATAAGAAAAAAGAAGAAACGAA
```

Fig. 10B

```
SAK   GTCTTTCCCTATAACAGAAAAAGGTTTTGTTGTCCCAGATTTATCAGA
SAK-1 GTCTTTCCCTATAACAGAAAAAGGTTTTGTTGTCCCAGATTTATCAGA
SAK-2 GTCTTTCCCTATAACAGAAAAAGGTTTTGTTGTCCCAGATTTATCAGA

SAK   GCATATTAAAAACCCTGGATTCAACTTAATTACAAAGGTTGTTATAG
SAK-1 GCATATTAAAAACCCTGGATTCAACTTAATTACAAAGGTTGTTATAG
SAK-2 GCATATTAAAAACCCTGGATTCAACTTAATTACAAAGGTTGTTATAG

SAK   AAAAGAAATAA
SAK-1 AAAAGAAATAAAACAAAATAGTTGTTTATTATAGAAAGTAATGTC
SAK-2 AAAAGAAATAAAACAAAATAGTTGTTTATTATAGAAAGTAATGTC

SAK-1 TTGATTGAATATGTGTAGTGAAATTATCTTTCATCAAATTCTCATT
SAK-2 TTGATTGAATATGTGTAGTGAAATTATCTTTCATCAAATTCTCATT

SAK-1 CATGCACGAATGGTTCTGCCCCACCTAATCAGATATTACGTGACT
SAK-2 CATGCACGAATGGTTCTGCCCCACCTAATCAGATATTACGTGACT

SAK-1 TATGGGGAGAAATCAGTTTGGATAAAAGTGGAGGATCCAGTAGCC
SAK-2 TATGGGGAGAAATCAGTTTGGATAAAAGTGGAGGATCCAGTAGCC

SAK-1 G
SAK-2 G
```

Fig. 11 Modification of SAK in SAK-2

```
         1         10        20        30        40
SAK    SSSFDKGKTKKGDDASYFEPTGPYLMVNVTGVDGKGNELLSPHYVEFP
SAK-2     AGATKKGDDASYFEPTGPYLMVNVTGVDGKGNELLSPHYVEFP 50        60        70        80        90
SAK    IKPGTTLTKEKIEYYVEWALDATAYKEFRVVELAPSAKIEVTYYDKNKK
SAK-2  IKPGTTLTKEKIEYYVEWALDATAYKEFRVVELAPSAKIEVTYYDKNKK 100       110       120       130   136
SAK    EETTKSFPITEKGFVVPDLSEHIKNPGFNLITKVVIEKK
SAK-2  EETTKSFPITEKGFVVPDLSEHIKNPGFNLITKVVIEKK
```

METHOD FOR OXYGEN REGULATED PRODUCTION OF RECOMBINANT STAPHYLOKINASE

This application claims the benefit of U.S. Provisional Application No. 60/459,439 filed Apr. 1, 2003 and incorporates the same by reference.

FIELD OF THE INVENTION

The present invention, disclosed herein, relates to a novel process for the production of staphylokinase (SAK) and its derivatives by modulating the level of oxygen of its growth medium using a genetically engineered strain of E. coli. The invention includes DNA sequences that encode for the staphylokinase forms according to the invention and recombinant plasmids on which these DNA sequences are present coupled with a highly effective expression signal that is controlled by the supply of oxygen.

The overall process concerns a new method for the high yield production of staphylokinase and its analogs using a specifically designed protein expression signal that does not require use of any expensive exogenous chemicals to induce the protein production and, therefore, provides an economic advantage over the currently known procedure for the production of staphylokinase. The staphylokinase and its derivatives produced via this process display specific clot lysis activity and human plasminogen activation capability that is comparable to its native counterpart. Thus, in principle, the present process constitutes a new and more economical means for the production of staphylokinase and its derivatives that may be useful in thrombolytic therapy.

In conjunction with this, the invention also comprises the design of a novel DNA sequence compatible with the SAK encoding DNA sequence that results in the accumulation of Staphylokinase protein in large amounts within the cell when oxygen concentration is lower than 2% of total atmospheric oxygen or cells attain stationary phase of their growth. The SAK forms produced according to the invention are thus suitable as pharmaceutical preparations in humans for the treatment of thromboembolic angioses.

BACKGROUND OF THE INVENTION

Staphylokinase, an extracellular protein of several strains of Staphylococcus aureus, is a promising blood-clot dissolving agent that carries many desirable thrombolytic properties and is useful for the treatment of patients suffering from thromboembolic disorders and myocardial infarcation [Collen et. al., Fibrinolysis, vol. 6; 232-242, 1992; Collen et. al., vol. 87, 996-1006, 1993]. It forms a bimolecular complex with the blood proteins, such as plasminogen (PG) and plasmin (Pm) and exerts its fibrinolytic effects through conversion of an active non specific serine protease, plasmin (Pm) to a highly specific proteolytic enzyme that can recognize blood zymogen, PG, as a substrate and convert it into plasmin that is capable of degrading blood clots. In a plasma milieu, SAK, is able to dissolve fibrin clots without any associated fibrinogen degradation [Collen et. al., J. Biol. Chem. 268, 8284-8289, 1993; Lijnen et. al., J. Biol. Chem. 266, 11826-11823]. This fibrin-specificity of SAK is the result of inhibition of staphylokinase-plasmin complex formation by alpha-2-antiplasmin during circulation in blood but highly diminished interaction with staphylokinase-plasmin complex at the fibrin surface, resulting in very localized plasminogen activation at the fibrin surface. In addition, staphylokinase has weak affinity for circulating plasminogen but a high affinity for fibrin-bound plasminogen. Recent clinical trials have shown that staphylokinase is as effective as t-PA at achieving early perfusion in myocardial infarction patients. Thus, its utility in thrombolytic treatment has now been established by several limited clinical trials [Collen et. al., Circulation, 87, 996-1006, 1993; Lijnen and Collen, Fibrinolysis, 10, 119-126, 1996].

Staphylokinase is a single chain 16 kD protein, consisting of 136 amino-acid residues It is produced in very low amounts by its natural host, Staphylococcus aureus [Lack, Nature 161, 558-560, 1948; Robbinson et. al., J. Biol. Chem. 242, 2333-2342, 1967]. Production of intact, biologically active SAK from bacterial expression systems has been a challenge because of N-terminal micro-heterogeneity, plasmid instability, or low-production yield. Considering its therapeutic applicability and clinical implications in thrombolytic therapy, attempts have been made in the past (Gerlach et. al., Zbl. Bakt. Hyg. A269, 1988; Collen et. al., Fibrinolysis 6, 203-213, 1992) to search for an alternative source of SAK production through recombinant routes. The gene encoding for SAK has been isolated from its natural host, Staphylococcus aureus, and cloned into various heterologous hosts, e.g., E. coli, Bacillus and Yeast [Sako et. al., Mol. Gen. Genet., 190, 271-277, 1983]. In the case of Bacillus SAK appeared proteolytically degraded [Ruiqiong et. al., Biotechnol. Bioeng., 62, 87-96, 1998; Miele, et. al., J. Biol. Chem. 274, 7769-7776, 1999] and in Yeast it was found glycosylated that reduced the plasminogen-activation function of this protein. Therefore, these heterologous systems were not very suitable for the large scale production of this protein. In E. coli, extracellular production of SAK resulted in low level of SAK production carrying N-terminal degradation resulting in two forms of SAK. To overcome these problems, SAK encoding gene has been expressed using strong expression signals which required addition of exogenous inducers, such as IPTG, tryptophane, Indol-acetic acid etc. that makes these systems highly expensive when utilized for the large scale production of this protein. In this system, production of full length SAK was associated with a truncated form of SAK that lacked 10-N terminal amino acid residues of native SAK.

The present invention, therefore, is concerned with a new method for the high yield production of staphylokinase and its analogs using a new protein expression signal that does not require use of any expensive exogenous chemicals to induce the protein production and therefore provides an economic advantage over the currently known procedure for the production of staphylokinase. Moreover, the staphylokinase and its derivatives produced via this process display specific clot lysis activity and human plasminogen activation capability that is comparable to its native counterpart. Thus, in principle, the present process constitutes a new and more economical means for the production of staphylokinase and its derivatives that may be useful in thrombolytic therapy.

SUMMARY OF THE INVENTION

The prime objective of the present invention, therefore, is to develop biologically functional SAK analogs that do not exhibit N-terminal truncation and retained their full biological activity when produced at large scale.

Another objective of this process is to design and devise an efficient and economical production system for SAK and its variant that does not require use of any chemical inducer so that overall system can be economically viable.

Yet another objective of the invention is to prepare a piece of DNA carrying complete genetic information for the production of SAK in a suitable host such as *E. coli, Bacillus*, Yeast or any microbial system which has the characteristics of being modified as a host.

Yet another objective of the invention is to modify 1-10 amino-terminal amino acid residues of SAK to block its truncation during large scale production without affecting its overall functional activity.

Yet another objective of the invention to design a piece of DNA and integrate it with the DNA sequences of SAK to express SAK and N-terminally modified form of SAK for the high level expression of proteins.

Yet another objective of this invention is to prepare an expression plasmid DNA carrying the genetic information for the production of SAK inside the cell of recombinant *E. coli*.

SUMMARY OF THE INVENTION

The present invention relates to a nucleotide sequence of expression cassette OXY-1 of SEQ ID No. 1, a modified staphylokinase SAK-2 gene of SEQ ID No. 2, a peptide sequence of modified staphylokinase SAK-2 gene, of SEQ ID No. 3, three plasmids having International Deposition Nos BPL-0019, BPL-0020, and BPL-0021, and their corresponding three recombinant *E. Coli*, also invention relates to a process for over-producing staphylokinase and its analogues by modulating level of oxygen of its growth medium in a host system, and lastly, a method of dissolving blood clot in a subject in need thereof.

DETAILED DESCRIPTION OF THE PRESENT INVENTION

Accordingly, the present invention relates to a nucleotide sequence of expression cassette OXY-1 of SEQ ID No. 1, a modified staphylokinase SAK-2 gene of SEQ ID No. 2, a peptide sequence of modified staphylokinase SAK-2 gene, of SEQ ID No. 3, three recombinant *E. Coli* deposited in the Microbial Type Culture Collection at Institute of Microbial Technology, Chandigarh, India and having International Deposition Nos 5146, 5147 and 5148, and their corresponding three plasmids contained therein. Also, the invention relates to a process for over-producing staphylokinase and its analogues by modulating level of oxygen of its growth medium in a host system, and lastly, a method of dissolving blood clot in a subject in need thereof.

In an embodiment of the present invention, there is provided a nucleotide sequence of expression cassette OXY-1 of SEQ ID No. 1.

In another embodiment of the present invention, there is provided a modified staphylokinase SAK-2 gene of SEQ ID No. 2.

In yet another embodiment of the present invention, there is provided a peptide sequence of modified staphylokinase SAK-2 gene, of SEQ ID No. 3.

In still another embodiment of the present invention, there is provided a plasmid pRM1 having International Deposition No. BPL-0019.

In still another embodiment of the present invention, there is provided a plasmid pOXYSAK-1 having International Deposition No. BPL-0020.

In still another embodiment of the present invention, there is provided a plasmid pOXYSAK-2 having International Deposition No. BPL-0021.

In still another embodiment of the present invention, there is provided a recombinant *E. Coli* of International Deposition No. 5146, the International Depository is "Microbial Type Culture Collection" at Institute of Microbial Technology, Chandigarh, India, having a plasmid pRM1 of International Deposition No. BPL-0019.

In still another embodiment of the present invention, there is provided a recombinant *E. Coli* of International Deposition No. 5147, the International Depository is "Microbial Type Culture Collection" at Institute of Microbial Technology, Chandigarh, India, having a plasmid pOXYSAK-2 of International Deposition No. BPL-0020.

In still another embodiment of the present invention, there is provided a recombinant *E. Coli* of International Deposition No. 5148, the International Depository is "Microbial Type Culture Collection" at Institute of Microbial Technology, Chandigarh, India, having a plasmid pOXYSAK-2 of International Deposition No. BPL-0021.

In still another embodiment of the present invention, there is provided a process for over-producing staphylokinase and its analogues by modulating level of oxygen of its growth medium in a host system, said method comprising steps of:
  preparing a piece of DNA carrying genetic information for the production of staphylokinase,
  modifying 10 amino-terminal residues of SAK encoding DNA, wherein Lys6 and Lys8 residues of SAK are changed to small neutral amino-acid residues,
  constructing DNA expression cassette OXY-1,
  integrating the piece of DNA obtained at step (a) or step (b) with the OXY-1 to obtain pOXYPRO,
  transferring integrated product of step (d) on a plasmid vector to obtain plasmid construct pOXYSAK-1, and pOXYSAK-2 respectively,
  introducing the plasmid constructs of step (e) into a host system,
  culturing the host cell for over-production of SAK or its derivatives under high aeration and changing level of oxygen below 5% of atmospheric oxygen level when cell growth reaches to exponential phase to obtain cell mass,
  lysing the cells of step (g) to separating cell lysate from the cellular debris, and thereby obtaining the staphylokinase and its analogues.

In still another embodiment of the present invention, the Lys6 and Lys8 residues of SAK are changed into small and neutral amino acid residues.

In still another embodiment of the present invention, the plasmid vector is a high or medium copy number plasmid.

In still another embodiment of the present invention, the host system is selected from a group comprising *E. coli, Bacillus*, and Yeast.

In still another embodiment of the present invention, the sequence of OXY-1 is modified depending upon the host system.

In still another embodiment of the present invention, the amino acids are selected from a group comprising Alanine, and Glycine.

In still another embodiment of the present invention, the growth medium is Luria Broth (LB) medium.

In still another embodiment of the present invention, the host cell is cultured for over-production of SAK or its derivatives at shake flask culture or at fermentation.

In still another embodiment of the present invention, the host cell is cultured till O.D. 600 reaches 0.6 to 0.7.

In still another embodiment of the present invention, fermentation is carried out as a two-stage fed-batch fermentation.

In still another embodiment of the present invention, the cell mass is obtained by centrifugation or filtration.

In still another embodiment of the present invention, the cells are lysed by a method selected from a group comprising sonication, chemical, and mechanics lysis.

In still another embodiment of the present invention, the cell lysate is separated from the cellular debris by centrifugation.

In still another embodiment of the present invention, there is provided a method of dissolving blood clot in a subject in need thereof, said method comprising the step of administering pharmaceutically effective amount of streptokinase analogue SAK-2, optionally along with additive(s).

In still another embodiment of the present invention, the additive is selected from a group comprising nutrients consisting of proteins, carbohydrates, sugar, talc, magnesium stearate, cellulose, calcium carbonate, starch-gelatin paste, and/or pharmaceutically acceptable carrier, excipient, diluent, or solvent.

In still another embodiment of the present invention, the SAK-2 and additives are in a ratio ranging between 1:10 to 10:1.

Therefore, the present process pertains to the isolation of a piece of DNA from Staphylococcus aureus, carrying complete sequence for the production of SAK and its modification using known procedures [Sambrook et. al., Molecular Cloning: A laboratory Manual, 1989, Cold Spring Harbor] to produce SAK forms that lack N-terminal truncation resulting in single species of biologically active SAK. A newly designed piece of DNA has been constructed and linked with the SAK encoding DNA on a suitable plasmid vector, capable of replicating in an appropriate E. coli host, to produce a large amount of SAK and its analogs when the oxygen level of the growth condition is lower than 5% of atmospheric oxygen. Following these steps, high level SAK proteins can be obtained without showing any protein degradation.

The procedure described herein, for the production of SAK and its analogs, has not been known earlier, therefore, it provides a new, efficient and economical process for the production of biologically active SAK proteins simply by modulating the level of atmospheric oxygen in the culture medium in the shake flask culture or during fermentation regime. SAK or its analogs, thus produced, may be obtained by lysing the E. coli cells and separating the contaminating cellular proteins, following conventional chromatographic steps. Staphylokinase and its modified forms produced following these procedures are capable of exhibiting clot-lysis and plasminogen activation ability comparable to its natural counterpart and may find its utility in clinical medicine for the treatment of various circulatory disorders.

Accordingly, the present invention relates to a novel process for the production of staphylokinase and its derivatives by modulating the level of oxygen of its growth medium using a genetically engineered strain of E. coli and comprises:

(a) Preparation of a piece of DNA carrying genetic information for the production of staphylokinase through recombinant process or through a synthetic approach following known procedures, (b) modification of 10-amino acid residues of SAK encoding DNA where the Lys6 and Lys8 residues of SAK is changed such as Alanine, Glycine or similar small and neutral amino acid residues, (c) construction of synthetic DNA cassette carrying a defined DNA sequence (d) integration of a piece of DNA obtained at step (a) or step (b) with the DNA sequence made at step (C) following the conventional method of recombinant technology, (e) transfer of the SAK encoding sequences linked with the specific protein expression signal made at step (d) on a suitable replicating plasmid vector following known recombinant DNA techniques, (f) a suitable plasmid vector in such case could be a high or medium copy number plasmids, specific to a host system, (g) introducing the plasmid constructs containing the SAK encoding plasmids obtained at step (e) into an appropriate host, such as E. coli, Bacillus, Yeast or any microbial system that has a characteristic of being modified as a host, (h) culturing the host cells harboring the expression plasmid for the production of SAK or its modified forms either at shake flask culture at high aeration or at fermentation level till the O.D.600 reaches 0.6 to 0.7 and then lower down the oxygen level that constitute less than 5% of the total atmospheric oxygen, (i) removing the cells by centrifugation, filtration and the like, and lysing the cells by conventional procedures, such as sonication, chemical or mechanical lysis followed by separating the cell lysate from the cellular debris after centrifugation and subsequently purifying the staphylokinase using known procedures.

The details of the present invention are:

The overall process developed and disclosed herein is based on the use of a new DNA sequence (FIG. 3) linked with the SAK and SAK forms that allows production of large amounts of staphylokinase by changing the oxygen parameters of the culture condition and does not require use of any external source to induce the production of recombinant SAK in E. coli.

Use of E. coli as host for high level production of recombinant proteins is widespread in modern biotechnological practices. Large scale production of useful proteins is typically achieved via two-stage fed-batch fermentations. In the first stage of such a process, cells are grown to a high cell density under reasonably balanced growth conditions. This requires that the synthesis of the heterologous proteins be minimized. In the second stage, high level expression of the recombinant proteins is activated. It is also recognized that the relative performance of different promoters varies from protein to protein. The properties of the promoter that regulates the expression of the recombinant protein are therefore crucial for the process productivity. Previously, SAK encoding gene has been cloned under inducible promoters, e.g., tac or T7 that required use of a gratuitous inducer molecule or increasing the temperature of the growth conditions. Whereas, the former approach tends to interfere less with host cell metabolism, gratutious inducers are generally expensive and hence affect the economics of scale up. Also, native SAK gene when integrated with these expression systems exhibited processing of the N-terminal region of SAK resulting in microheterogeneity in the protein product. Therefore, the modification of Lys6 and Lys 8 amino acid residues were made at the N-terminal sequence to block the N-terminal processing of SAK without affecting its overall functional properties. When these SAK forms were linked with the newly designed DNA expression sequences, they were able to produce a large amount of SAK in cell culture of E. coli.

The novel SAK expression system was developed using the prototype SAK expression system pRM1 (FIG. 1, [Rajamohan and Kanak L. Dikshit, FEBS Letters 474, 151-158, 2000]) that carries SAK encoding gene under the IPTG inducible T7 promoter and a novel protein expression cassette (FIG. 3) that carries DNA sequence for the binding of oxygen sensitive regulatory proteins such as FNR (Ferredoxin-NADP+ reductase) at a specific position. SAK encoding gene (FIG. 4) was linked with the protein expression cassette using recombinant DNA techniques and this fusion product was subsequently cloned on a suitable replicating plasmid vector (FIGS. 7 and 8) to generate SAK expression plasmid vector carrying SAK gene or its modified forms (FIG. 6, FIG. 9) under the novel expression cassette, designated as pOXYPRO (FIG. 6) that is activated for the protein expression when the oxygen level is low (~less than 5% of atmospheric oxygen).

In a preferred embodiment, the present invention discloses the design of a plasmid vector that utilizes the fusion of a novel protein expression sequence (FIG. 3) with the DNA sequences of SAK (FIG. 4) or its N-terminally modified forms (FIG. 5 and FIG. 6) to produce a large amount of staphylokinase or its analogs when the oxygen level of its growth condition goes below 5% of atmospheric oxygen level.

In yet another preferred embodiment of the process of the present invention, a synthetic cassette carrying a defined DNA sequence (FIG. 3) was made using a known procedure and joined at the N-terminus of SAK encoding DNA and cloned on a suitable plasmid which could be pUC or Bluescript.

In another preferred embodiment E. coli strain has been utilized for the SAK expression plasmid vectors (FIG. 8 and FIG. 9) encoding SAK or SAK forms.

The invention is illustrated by the following examples which, however, should not be taken in a restrictive sense. The processes are given by way of illustration of the present invention, and therefore, should not be construed to limit the scope of the present invention.

General Methods Utilized in the Examples

1. Recombinant DNA techniques: Conventional and well known techniques of recombinant DNA and molecular biology were utilized. Details of these techniques are available in various standard text books or manuals related to this field for example, Sambrook et. al., Molecular Cloning: A Laboratory Manual (2$^{nd}$ edition, Cold spring Harbor Press, New York, 1989).

2. Electrophoretic analysis of proteins: Purified preparation of SAK or its presence in vivo was analysed through SDS-PAGE, essentially according to Laemmli procedure (Nature 227; 680, 1970).

3. Casein-Plasminogen overlay assay for detection of in vivo SAK activity: Bacterial colonies producing staphylokinase can be routinely detected by overlay of casein and human plasminogen in soft agar following the procedure of Malke, H. and Ferreti, J. J. (Proc. Natl. Acad. Sc. 81; 3557, 1984). Briefly, 10 ml of soft agarose mixture carrying 0.8% agarose, 10% skim milk, 100 μg of human plasminogen, 150 mM NaCl and 50 mM Tris-Cl (pH.8.0) is poured on top of plates carrying bacterial colonies expressing staphylokinase. These plates were incubated at 37° C. for 4-5 h and SAK carrying colonies were identified by the presence of a clearing zone around the colonies.

4. Assay for Staphylokinase using chromogenic peptide substrate. Plasminogen activation ability of staphylokinase and its modified forms were checked through known procedures (Methods of Enzymology; 80; 387). Briefly, one microliter of appropriately diluted sample of SAK was mixed with 25 μl of sample buffer (0.15 M Tris. Cl, pH 7.5) and 100 μg of human plasminogen and incubated at 37° C. for 15 minutes and then 18 μl of NaCl (1.77 M in 0.032 M Tris. Cl, pH 7.5) is added. The amount of plasmin thus generated was measured after addition of 12 μl of chromogenic substrate, Chromozyme PL (5 mg/ml in water, Boehringer Mannheim), and tubes were further incubated at 37° C. for 10 minutes. SAK activity was measured at 405 nm due to the release of yellow colored p-4-nitroaniline.

Clot lysis assay: Clot lysis ability of SAK or its modified forms was tested following the standard methods (British Pharmacopia, 1980 edition). Fibrin clot lysis was carried out in the presence of citrated human plasma or human fibrinogen containing different concentrations of SAK or its analogs. Briefly, fibrin clot was labelled by radioiodination ($^{125}$I) and mixed with appropriate concentrations of SAK and incubated at 37° C. and rotated slowly. 0.1 ml aliquot was removed at regular intervals and release of soluble fibrin was measured by the amount of radioactivity released using gamma counter.

BRIEF DESCRIPTION OF THE ACCOMPANYING DRAWINGS

1. FIG. 1: Map of plasmid pRM1
2. FIG. 2 Sequence of oligonucleotide to construct the protein expression cassette
3. FIG. 3 Complete nucleotide sequence of expression cassette, OXY-1
4. FIG. 4. Nucleotide sequence of SAK gene (SEQ ID NO: 8)
5. FIG. 5. Nucleotide sequence encoding SAK1 protein (SEQ ID NO: 9)
6. FIG. 6. Nucleotide sequence encoding SAK2 protein (SEQ ID NO: 2)
7. FIG. 7. Schematic representation of construction of plasmid, pOXYPRO, carrying OXY-1 expression cassette
8. FIG. 8. Construction and map of plasmid, pOXYSAK-1 containing SAK-1 gene under OXY-1 expression cassette.
9. FIG. 9. Construction and map of plasmid, pOXYSAK-2 containing SAK2 gene under OXY-1 expression cassette.
10. FIGS. 10A-B Sequences of SAK (SEQ ID NO: 8), SAK-1 (SEQ ID NO: 9) and SAK-2 (SEQ ID NO:2) genes. Terminator sequence in SAK-1 and SAK-2 are shown in bold letters and modified residues in SAK-2 are shown in small bold letters.
11. FIG. 11. Modification of SAK in SAK-2 (SEQ ID NO: 3). Modified residues are shown in bold letters.

The invention is further elaborated with the help of examples. However, the examples should not be construed to limit the scope of the Invention

EXAMPLE 1

Construction of Expression System for the Production of intracellular Staphylokinase The overall process for the construction of expression system for the production of Staphylokinase basically involved following three main steps:

Step 1: In order to construct a recombinant plasmid able to produce native-like recombinant SAK, total genomic DNA was isolated from a locally isolated species of *Staphylococcus aureus* (designated as SAK-11) using standard DNA isolation procedure. First SAK encoding DNA sequence was amplified through PCR using following set of oligonucleotide primers

```
SAK-1 primer:
5'-GATTGTAGCCATATGTCAAGTTCATTCGACAAAGGAA-3'
(37-mer).

SAK-2 primer:
5'-CGGCTACTGGATCCTCCACTTTTATCCAAACTGATTT-3'
(37-mer).
```

The PCR was carried out using the DNA template of *S. aureus* and SAK-1 and SAK-2 primers in 100 ul reaction mixture carrying 10 nanograms of template DNA, 20 picomoles of SAK-1 and SAK2, 2.5 units of Vent DNA polymerase (NEB) and 20 μL of each dNTPs and 10 μl of standard PCR buffer (10× buffer; commercially available from NEB). A total number of 30 cycles and a final extension of 10 minutes at 72° C. was used for PCR. It resulted in 606 bp amplified DNA product as observed on 1% agarose gel. This DNA product was digested with restriction enzymes, cloned at NdeI and BamHI site of pET9b plasmid vector, and the presence of SAK gene on the recombinant plasmid was further verified by nucleotide sequence analysis (FIG. 4) by following standard recombinant DNA techniques. It resulted in construction of a plasmid vector, pRM1 (deposited as BPL-0019 in Microbial Type Culture Collection, a national culture depository located at the Institute of Microbial Technology, Chandigarh, a constituent laboratory of Council of Scientific and Industrial Research. BPL stands for the plasmid in bacteria and 0019 denotes the serial number of deposited material).

Glycerol stocks of *E. coli* carrying recombinant plasmid, pRM1 (FIG. 1) was made as described in standard recombinant DNA text book (Sambrook et. al., Molecular Cloning: A laboratory Manual 1989; Cold Spring Harbor) and maintained at −70° C. To prepare the biologically active Staphylokinase, a seed culture of recombinant bacteria carrying SAK expression plasmid, pRM1, was raised by inoculating freshly thawed glycerol stock into 100 ml of standard Luria Broth (LB) medium (in a 500 ml conical flask) containing 25 μg/ml Kanamycin sulphate.

Step 2: The second step involves construction of a synthetic DNA cassette, OXY-1 for the expression of SAK and its derivatives. The construction of 150 base DNA cassette, OXY-1, was synthesized using synthetic oligonucleotides. These oligonucleotides were synthesized commercially and their sequence is given in FIG. 2. 1 μg of each oligonucleotide was mixed together and heated in a water bath at 100° C. for 2 min and thereafter cooled down slowly at room temperature for 30 min. The annealing mixture so obtained was run on a 2% agarose gel and 150 base DNA band was gel purified using commercially available DNA purification kits (Wizard DNA purification kit, Promega Biotech). This 150 base purified DNA fragment was digested with restriction enzymes Hind III and BamHI and joined on plasmid vector pUC18 (New England Bio labs) at HindIII-BamHI site. The resulting plasmid vector was designated as pOXY-1 (FIG. 7). The entire sequence of 150 base DNA inserted on pUC18 was checked through nucleotide sequence analysis and is depicted in FIG. 3.

Step 3. The third step involves construction of expression plasmid vector, pOXYSAK-1 (deposited as BPL-0020 in Microbial Type Culture Collection, a national culture depository located at the Institute of Microbial Technology, Chandigarh), carrying novel expression signal for the intracellular production of SAK in *E. coli*. Construction of the plasmid vector encoding SAK under the control of oxygen-regulated protein expression signal was done by retrieving SAK encoding DNA from the plasmid, pRM1 (described in step 1, FIG. 1) and combining it with the novel protein expression signals of plasmid, pOXYPRO resulting in the plasmid vector, pOXYSAK-1. Schematic construction of plasmid, pOXYSAK-1, is depicted in FIG. 8. SAK encoding DNA sequence was amplified through PCR from pRM1 using the following set of oligonucleotide primers

```
SAK-3 primer:                              (SEQ ID NO: 6)
5'-GAACTTAAGGAAGATATACATATGTCAAGTTCATTCGACAA AGGA-
3' (45 mer)

SAK-2 primer:                              (SEQ ID NO: 5)
5'-CGGCTACTGGATCCTCCACTTTTATCCAAACTGATTT-3'
(37 mer)
```

The PCR was carried out using the DNA template of pRM1 and SAK-3 and SAK-2 primers in 100 μl reaction mixture carrying 10 nanograms of template DNA, 20 picomoles of SAK-1 and SAK2, 2.5 units of Vent DNA polymerase (NEB) and 20 μl of each dNTPs and 10 μl of standard PCR buffer (10× buffer; commercially available from NEB). A total number of 30 cycles and a final extension of 10 minutes at 72° C. was used for PCR. It resulted in 606 bp amplified DNA product as observed on 1% agarose gel. This DNA product was digested with restriction enzymes and cloned at AflII and BamHI site of OXY-1 plasmid vector following the standard recombinant DNA techniques.

In a separate set 2 μg of plasmid DNA pOXYPRO, prepared at step 2, was digested with 2 units each of Afl II and BamHI restriction enzyme at 37° C. for two hours and mixed up with the 606 base gel purified fragment carrying entire SAK gene. This mixture of DNA was precipitated by adding 2× volume of absolute alcohol and incubating it at −20° C. for 1 h. The DNA was recovered after centrifugation of this mixture for 20 min at 14000 rpm. Supernatant was discarded and a pellet was dissolved in 17 μl of water. DNA mixture was then ligated in the presence of 10 units of DNA ligase and 1× ligase buffer (New England Biolabs) at 20° C. for overnight. For the transformation step, approx. 100 ng of the ligated DNA was used to transform *E. coli* JM105 electrocompetant cells and transformed cells were plated on LB-Amp plates. 10 transformed colonies of *E. coli* were picked up and their plasmid DNA were analysed for the presence of 606 base DNA insert carrying an entire SAK encoding gene under the OXY-1 signal sequence. Presence of the SAK gene on the recombinant plasmid was further verified by nucleotide sequence analysis and designated as pOXYSAK-1 (FIGS. 5, 9).

EXAMPLE 2

Production of Recombinant Staphylokinase from *E. coli*

For the production of recombinant staphylokinase in *E. coli* using recombinant plasmid, pOXYSAK (FIG. 8), glycerol stocks of *E. coli* JM109 strain harboring plasmid, pOXYSAK-1, maintained at −70° C. were used to prepare a seed culture by inoculating freshly thawed glycerol stock (approx. 100 ul) into a 500 ml flask carrying 100 ml of LB medium with 100 μg/ml of ampicillin. The flask was incubated at 37° C. with shaking on a rotary shaker at 200 rpm for 16-18 h. This cell culture of *E. coli* was used to seed four 2 Liter Erlenmyer flasks each containing 500 ml of the same medium (LB containing 100 μg/ml ampicillin) using 5% of the inoculum. The flasks were incubated at 37° C. with shaking at 200 rpm until the absorbance of the culture at 600 nm reached to 0.8 (around 5-6 h after inoculation). Thereafter, shaking of the culture was changed to 50 rpm and the culture was allowed to grow for another 6-8 h to build up the SAK protein inside the cells.

EXAMPLE 3

Recovery of Recombinant SAK from *E. coli*, Purification and Characterization of its Biological Activity The 6-8 h grown *E. coli* cells, carrying pOXYSAK (as mentioned in Example 2), were harvested by spinning them down by centrifugation at 6000×g in a GS-3 rotor (Sorvall) for 30 min at 4° C. The supernatants were discarded and the cell pellet was resuspended in 50 ml of Tris.Cl buffer and lysed either by sonication or chemical lysis using 6M guanidium hydrochloride and 20 mM sodium phosphate buffer, pH 7.2. The cell lysate was centrifuged at 6000×g at 4° C. for 15 min and clear lysates were diluted four fold with distilled water and thereafter applied at room temperature to a 10×32 cm column of SP-sepharose at a flow rate of 1 liter per hour. The column was washed with 0.1M phosphate buffer, pH 6.2 and eluted with a gradient of 0.1 to 0.5M NaCl. The SAK containing fraction was checked by spot test by mixing 1 ul of fraction with 1 μl of human plasminogen (100 mg/ml) and 1 μl of chromozyme PL. The SAK containing fractions exhibited development of yellow color. These fractions were pooled and adjusted to 2.5 M with solid sodium chloride and subjected to hydrophobic interaction chromatography on a 10×20 cm column of phenyl-sepharose at room temperature and flow rate of 1 liter/hour. The column was washed with 0.1M phosphate buffer and SAK was eluted with 0.01M phosphate buffer (pH 6.2). Aliquots from each fraction were analyzed on 15% SDS-PAGE to examine the relative purity of the eluted protein. On SDS-PAGE, it showed a single band of 16 kD. Specific activity of purified SAK protein was estimated as 1.75 U/μg protein that was comparable to native SAK.

EXAMPLE 4

Production of N-Terminally Modified SAK-Derivative Under OXYPRO Expression Signal A SAK derivative that carry modified amino terminus but retained its full biological activity was designed and fused with the OXYPRO sequences to overcome the problem of N-terminal processing of SAK that has been observed usually during large scale production of SAK.

5 N-terminal residues were deleted and Lys6 and Lys8 were replaced with Ala. Total genomic DNA of *Staphylococcus aureus* (SAK-11 as mentioned in Example 1, step 1) was isolated and used as a template for the PCR amplification using following set of oligonucleotide primers:

```
SAK 4 primer:                           (SEQ ID NO: 7)
5'-GAACTTAAGCATATGGCTGGAGCTTATAAAAAGGGC-3'

SAK 2 primer:                           (SEQ ID NO: 5)
5'-CGGCTACTGGATCCTCCACTTTTATCCAAACTGATTT-3'
```

The PCR was carried out using 10 nanograms of template DNA, 20 picomoles of SAK-4 and SAK-2 primers, 2.5 units of Vent DNA polymerase and 20 units of dNTPs and 10 μl of commercially available standard PCR buffer (New England Biolabs). A total number of 30 cycles and a final extension of 10 minutes at 72° C. were used for PCR. It resulted in a nearly 581 base pair amplified DNA product as observed on 1% agarose gel. This amplified DNA product was digested with restriction enzymes AflII and BamHI. In a parallel set 2 μg of plasmid DNA of pOXYPRO was digested with 4 units of restriction enzymes AflII and BamHI at 37° C. for 2 h in the presence of commercially available multicore buffer (New England Biolabs) and mixed with PCR amplified DNA and ethanol precipitated at by adding double volume of absolute of alcohol and one tenth volume of Sodium acetate (0.5M) and keeping it at 4° C. for 2 hours. The precipitated DNA was recovered after centrifugation of this mixture for 20 minutes at 14000 rpm. Supernatant was discarded and pellet was dissolved in 17 μl of water. This mixture was then ligated in the presence of 10 units of DNA ligase and 1 μl of DNA ligase buffer at 20 C overnight. After that, approx 10 ng of this ligated DNA was used to transform *E. coli* JM105 eletrocompetant cells using standard procedure. Transformed cells were plated on LB plates carrying 100 μg ampicillin/ml. After overnight incubation at 37° C., several colonies appeared on the plates and out of those, 10 colonies were analyzed for the presence of 430 base DNA insert carrying modified SAK gene i.e. SAK-2. 591 base DNA encoding modified SAK gene was sequenced and its sequence is given in FIG. 6. This plasmid construct was designated as pOXYSAK-2 (FIG. 9). This plasmid vector has been deposited in Microbial Type Culture Collection as BPL-0021.

*E. coli* JM105 carrying pOXYSAK-2 was grown into 500 ml flask carrying 100 ml LB-medium with 100 μg/ml of ampicillin and incubated at 37° C. with shaking on a rotary shaker at 200 rpm for 5-6 hr till the absorbance of the culture at 600 nm reached to 0.8. Thereafter shaking of the culture was changed to 50 rpm and the culture was allowed to grow for another 6-8 hr. From this culture, SAK was purified following the steps described in Example 3. SDS-PAGE analysis of purified protein preparation indicated the presence of a single band corresponding to 16 kD. Specific activity of purified SAK protein was estimated as 1.70,000 U/mg of protein that was comparable to the purified preparation of standard SAK obtained from the native host, *S. aureus*.

The invention claimed is:

1. A recombinant nucleotide sequence of expression cassette OXY-1 of SEQ ID No. 1.

2. A recombinant nucleotide sequence that encodes staphylokinase SAK-2 protein of SEQ ID NO: 3.

3. A plasmid comprising the recombinant nucleotide sequence of claim 1.

4. A plasmid pOXYSAK-1 contained in E. coli of International Deposition No. 5147 in the "Microbial Type Culture Collection" at Institute of Microbial Technology, Chandigarh, India.

5. A plasmid pOXYSAK-2 contained in E. coli of International Deposition No. 5148 in the "Microbial Type Culture Collection" at Institute of Microbial Technology, Chandigarh, India.

6. A recombinant E. coli of International Deposition No. 5146, in the "Microbial Type Culture Collection" at Institute of Microbial Technology, Chandigarh, India.

7. A recombinant E. coli of International Deposition No. 5147, deposited in the International Depository "Microbial Type Culture Collection" at Institute of Microbial Technology, Chandigarh, India.

8. A recombinant E. coli of International Deposition No. 5148, deposited in the International Depository is "Microbial Type Culture Collection" at Institute of Microbial Technology, Chandigarh, India.

9. A recombinant nucleotide sequence of claim 2, wherein the nucleotide sequence comprises nucleotides 1-582 of SEQ ID NO: 2.

10. A recombinant nucleotide sequence of claim 9 consisting of nucleotides 1-582 of SEQ ID NO: 2.

11. A plasmid as claimed in claim 3, wherein the plasmid is plasmid pRM1 contained in E. coli of International Deposition No. 5146 in the "Microbial Type Culture Collection" at Institute of Microbial Technology, Chandigarh, India.

* * * * *

SEQUENCE LISTING

```
<160> NUMBER OF SEQ ID NOS: 14

<210> SEQ ID NO 1
<211> LENGTH: 161
<212> TYPE: DNA
<213> ORGANISM: Artificial Sequence
<220> FEATURE:
<223> OTHER INFORMATION: A nucleotide sequence of expression cassette
```

-continued

OXY-1

<400> SEQUENCE: 1
gatcaagctt atcatcgata agcttacagg acgctgggtt aaaagtattt gagttttgat    60
gtggattaag ttttgagagg tcaataagat tataatatgt gatgcttcac aattctgatg   120
tatggcaaaa ccataataat gaacttaagg aagacctcat g                       161

<210> SEQ ID NO 2
<211> LENGTH: 582
<212> TYPE: DNA
<213> ORGANISM: Artificial Sequence
<220> FEATURE:
<223> OTHER INFORMATION: A modified staphylokinas SAK-2 gene

<400> SEQUENCE: 2
gaacttaagc atatgaaagg aaaatataaa aagggcgatg acgcgagtta ttttgaacca    60
acaggcccgt atttgatggt aaatgtgact ggagttgatg gtaaaggaaa tgaattgcta   120 tccccctcatt atgtcgagtt tcctattaaa cctgggacta cacttacaaa agaaaaaatt   180
gaatactatg tcgaatgggc attagatgcg acagcatata aagagtttag agtagttgaa   240
ttagatccaa gcgcaaagat cgaagtcact tattatgata agaataagaa aaagaagaa    300 acgaagtctt tccctataac agaaaaaggt tttgttgtcc cagatttatc agagcatatt   360
aaaaaccctg gattcaactt aattacaaag gttgttatag aaaagaaata aacaaaata    420 gttgtttatt atagaaagta atgtcttgat tgaatatgtg tagtgaaatt atctttcatc   480
aaattctcat tcatgcacga atggttctgc cccacctaat cagatattac gtgacttatg   540
gggagaaatc agtttggata aaagtggagg atccagtagc cg                      582

<210> SEQ ID NO 3
<211> LENGTH: 363
<212> TYPE: PRT
<213> ORGANISM: Artificial Sequence
<220> FEATURE:
<223> OTHER INFORMATION: A peptide sequence of modified staphylokinas
      SAK-2 gene

<400> SEQUENCE: 3

Glu Ala Leu Ala Gly Leu Tyr Ala Leu Ala Thr His Arg Leu Tyr Ser
1               5                   10                  15

Leu Tyr Ser Gly Leu Tyr Ala Ser Pro Ala Ser Pro Ala Leu Ala Ser
            20                  25                  30

Glu Arg Thr Tyr Arg Pro His Glu Gly Leu Pro Arg Thr His Arg Gly
        35                  40                  45

Leu Tyr Pro Arg Thr Tyr Arg Leu Glu Met Glu Thr Val Ala Leu Ala
    50                  55                  60

Ser Asn Val Ala Leu Thr His Arg Gly Leu Tyr Val Ala Leu Ala Ser
65                  70                  75                  80

Pro Gly Leu Tyr Leu Tyr Ser Gly Leu Tyr Ala Ser Asn Gly Leu Leu
                85                  90                  95

Glu Leu Glu Ser Glu Arg Pro Arg His Ile Ser Thr Tyr Arg Val Ala
            100                 105                 110

Leu Gly Leu Pro His Glu Pro Arg Ile Leu Glu Leu Tyr Ser Pro Arg
        115                 120                 125

Gly Leu Tyr Thr His Arg Thr His Arg Leu Glu Thr His Arg Leu Tyr
    130                 135                 140

Ser Gly Leu Leu Tyr Ser Ile Leu Glu Gly Leu Thr Tyr Arg Thr Tyr

```
                 145                 150                 155                 160
Arg Val Ala Leu Gly Leu Thr Arg Pro Ala Leu Ala Leu Glu Ala Ser
                165                 170                 175
Pro Ala Leu Ala Thr His Arg Ala Leu Ala Thr Tyr Arg Leu Tyr Ser
                180                 185                 190
Gly Leu Pro His Glu Ala Arg Gly Val Ala Leu Val Ala Leu Gly Leu
                195                 200                 205
Leu Glu Ala Leu Ala Pro Arg Ser Glu Arg Ala Leu Ala Leu Tyr Ser
                210                 215                 220
Ile Leu Glu Gly Leu Val Ala Leu Thr His Arg Thr Tyr Arg Thr Tyr
225                 230                 235                 240
Arg Ala Ser Pro Leu Tyr Ser Ala Ser Asn Leu Tyr Ser Leu Tyr Ser
                245                 250                 255
Gly Leu Gly Leu Thr His Arg Thr His Arg Leu Tyr Ser Ser Glu Arg
                260                 265                 270
Pro His Glu Pro Arg Ile Leu Glu Thr His Arg Gly Leu Leu Tyr Ser
                275                 280                 285
Gly Leu Tyr Pro His Glu Val Ala Leu Val Ala Leu Pro Arg Ala Ser
                290                 295                 300
Pro Leu Glu Ser Glu Arg Gly Leu His Ile Ser Ile Leu Glu Leu Tyr
305                 310                 315                 320
Ser Ala Ser Asn Pro Arg Gly Leu Tyr Pro His Glu Ala Ser Asn Leu
                325                 330                 335
Glu Ile Leu Glu Thr His Arg Leu Tyr Ser Val Ala Leu Val Ala Leu
                340                 345                 350
Ile Leu Glu Gly Leu Leu Tyr Ser Leu Tyr Ser
                355                 360

<210> SEQ ID NO 4
<211> LENGTH: 37
<212> TYPE: DNA
<213> ORGANISM: Artificial Sequence
<220> FEATURE:
<223> OTHER INFORMATION: A primer SAK-1 for amplification

<400> SEQUENCE: 4
gattgtagcc atatgtcaag ttcattcgac aaaggaa                          37

<210> SEQ ID NO 5
<211> LENGTH: 37
<212> TYPE: DNA
<213> ORGANISM: Artificial Sequence
<220> FEATURE:
<223> OTHER INFORMATION: An oligonucleotide primer SAK-2

<400> SEQUENCE: 5
cggctactgg atcctccact tttatccaaa ctgattt                          37

<210> SEQ ID NO 6
<211> LENGTH: 45
<212> TYPE: DNA
<213> ORGANISM: Artificial Sequence
<220> FEATURE:
<223> OTHER INFORMATION: An oligonucleotide primer SAK-3

<400> SEQUENCE: 6
gaacttaagg aagatataca tatgtcaagt tcattcgaca aagga                 45

<210> SEQ ID NO 7
```

-continued

```
<211> LENGTH: 36
<212> TYPE: DNA
<213> ORGANISM: Artificial Sequence
<220> FEATURE:
<223> OTHER INFORMATION: An oligonucleotide primer SAK-4

<400> SEQUENCE: 7
gaacttaagc atatggctgg agcttataaa aagggc                                36

<210> SEQ ID NO 8
<211> LENGTH: 411
<212> TYPE: DNA
<213> ORGANISM: Staphylococcus aureu

<400> SEQUENCE: 8
tcaagttcat tcgacaaagg aaaatataaa aagggcgatg acgcgagtta ttttgaacca       60
acaggcccgt atttgatggt aaatgtgact ggagttgatg gtaaaggaaa tgaattgcta      120
tcccctcatt atgtcgagtt tcctattaaa cctgggacta cacttacaaa agaaaaaatt      180
gaatactatg tcgaatgggc attagatgcg acagcatata agagtttag agtagttgaa      240 ttagatccaa gcgcaaagat cgaagtcact tattatgata gaataagaa aaagaagaa       300 acgaagtctt tccctataac agaaaaaggt tttgttgtcc cagatttatc agagcatatt      360
aaaaaccctg gattcaactt aattacaaag gttgttatag aaaagaaata a               411

<210> SEQ ID NO 9
<211> LENGTH: 606
<212> TYPE: DNA
<213> ORGANISM: Staphylococcus aureus

<400> SEQUENCE: 9
gaacttaagg aagatataca tatgtcaagt tcattcgaca aaggaaaata taaaaagggc       60
gatgacgcga gttatttga accaacaggc ccgtatttga tggtaaatgt gactggagtt      120
gatggtaaag gaaatgaatt gctatcccct cattatgtcg agtttcctat aaacctggg      180 actacactta caaagaaaa aattgaatac tatgtcgaat gggcattaga tgcgacagca      240
tataaagagt ttagagtagt tgaattagat ccaagcgcaa agatcgaagt cacttattat      300
gataagaata gaaaaaga gaaacgaag tctttcccta acagaaaaa aggttttgtt       360 gtcccagatt tatcagagca tattaaaaac cctggattca acttaattac aaaggttgtt      420
atagaaaaga aataaaacaa atagttgtt tattatagaa agtaatgtct tgattgaata      480
tgtgtagtga aattatcttt catcaaattc tcattcatgc acgaatggtt ctgccccacc      540
taatcagata ttacgtgact tatggggaga aatcagtttg gataaaagtg gaggatccag      600
tagccg                                                                606

<210> SEQ ID NO 10
<211> LENGTH: 377
<212> TYPE: PRT
<213> ORGANISM: Staphylococcus aureus

<400> SEQUENCE: 10

Ser Glu Arg Ser Glu Arg Ser Glu Arg Pro His Glu Ala Ser Pro Leu
1               5                   10                  15

Tyr Ser Gly Leu Tyr Leu Tyr Ser Thr His Arg Leu Tyr Ser Leu Tyr
            20                  25                  30

Ser Gly Leu Tyr Ala Ser Pro Ala Ser Pro Ala Leu Ala Ser Glu Arg
        35                  40                  45
```

```
Thr Tyr Arg Pro His Glu Gly Leu Pro Arg Thr His Arg Gly Leu Tyr
 50                  55                  60
Pro Arg Thr Tyr Arg Leu Glu Met Glu Thr Val Ala Leu Ala Ser Asn
 65                  70                  75                  80
Val Ala Leu Thr His Arg Gly Leu Tyr Val Ala Leu Ala Ser Pro Gly
                 85                  90                  95
Leu Tyr Leu Tyr Ser Gly Leu Tyr Ala Ser Asn Gly Leu Leu Glu Leu
                100                 105                 110
Glu Ser Glu Arg Pro Arg His Ile Ser Thr Tyr Arg Val Ala Leu Gly
            115                 120                 125
Leu Pro His Glu Pro Arg Ile Leu Glu Leu Tyr Ser Pro Arg Gly Leu
        130                 135                 140
Tyr Thr His Arg Thr His Arg Leu Glu Thr His Arg Leu Tyr Ser Gly
145                 150                 155                 160
Leu Leu Tyr Ser Ile Leu Glu Gly Leu Thr Tyr Arg Thr Tyr Arg Val
                165                 170                 175
Ala Leu Gly Leu Thr Arg Pro Ala Leu Ala Leu Glu Ala Ser Pro Ala
            180                 185                 190
Leu Ala Thr His Arg Ala Leu Ala Thr Tyr Arg Leu Tyr Ser Gly Leu
        195                 200                 205
Pro His Glu Ala Arg Gly Val Ala Leu Val Ala Leu Gly Leu Leu Glu
    210                 215                 220
Ala Leu Ala Pro Arg Ser Glu Arg Ala Leu Ala Leu Tyr Ser Ile Leu
225                 230                 235                 240
Glu Gly Leu Val Ala Leu Thr His Arg Thr Tyr Arg Thr Tyr Arg Ala
                245                 250                 255
Ser Pro Leu Tyr Ser Ala Ser Asn Leu Tyr Ser Leu Tyr Ser Gly Leu
            260                 265                 270
Gly Leu Thr His Arg Thr His Arg Leu Tyr Ser Ser Glu Arg Pro His
        275                 280                 285
Glu Pro Arg Ile Leu Glu Thr His Arg Gly Leu Leu Tyr Ser Gly Leu
    290                 295                 300
Tyr Pro His Glu Val Ala Leu Val Ala Leu Pro Arg Ala Ser Pro Leu
305                 310                 315                 320
Glu Ser Glu Arg Gly Leu His Ile Ser Ile Leu Glu Leu Tyr Ser Ala
                325                 330                 335
Ser Asn Pro Arg Gly Leu Tyr Pro His Glu Ala Ser Asn Leu Glu Ile
            340                 345                 350
Leu Glu Thr His Arg Leu Tyr Ser Val Ala Leu Val Ala Leu Ile Leu
        355                 360                 365
Glu Gly Leu Leu Tyr Ser Leu Tyr Ser
    370                 375

<210> SEQ ID NO 11
<211> LENGTH: 50
<212> TYPE: DNA
<213> ORGANISM: Artificial Sequence
<220> FEATURE:
<223> OTHER INFORMATION: An oligonucleotide PEC-2 for preparing protein
      expression cassette

<400> SEQUENCE: 11
gatcaagctt atcatcgata agcttacagg acgctgggtt aaaagtattt            50

<210> SEQ ID NO 12
<211> LENGTH: 55
```

```
-continued

<212> TYPE: DNA
<213> ORGANISM: Artificial Sequence
<220> FEATURE:
<223> OTHER INFORMATION: An oligonucleotide PEC-2 for preparing protein
      expression cassette

<400> SEQUENCE: 12
atcttattga cctctcaaaa cttaatccac atcaaaactc aaatactttt aaccc        55

<210> SEQ ID NO 13
<211> LENGTH: 55
<212> TYPE: DNA
<213> ORGANISM: Artificial Sequence
<220> FEATURE:
<223> OTHER INFORMATION: An oligonucleotide PEC-3 for preparing protein
      expression cassette

<400> SEQUENCE: 13
agaggtcaat aagattataa tatgtgatgc ttcacaattc tgatgtatgg caaaa        55

<210> SEQ ID NO 14
<211> LENGTH: 50
<212> TYPE: DNA
<213> ORGANISM: Artificial Sequence
<220> FEATURE:
<223> OTHER INFORMATION: An oligonucleotide PEC-4 for preparing protein
      expression cassette

<400> SEQUENCE: 14
atgaggtctt ccttaagttc attattatgg ttttgccata catcagaatt              50
```